United States Patent
Paul et al.

(10) Patent No.: US 10,688,262 B2
(45) Date of Patent: Jun. 23, 2020

(54) CONFIGURATION OF RESPIRATORY THERAPY MODES

(75) Inventors: Zachary Dean Paul, Pittsburgh, PA (US); Mark Dominic D'Angelo, Harrison City, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 404 days.

(21) Appl. No.: 14/122,458

(22) PCT Filed: Jun. 4, 2012

(86) PCT No.: PCT/IB2012/052798
§ 371 (c)(1),
(2), (4) Date: Nov. 26, 2013

(87) PCT Pub. No.: WO2012/168848
PCT Pub. Date: Dec. 13, 2012

(65) Prior Publication Data
US 2014/0102454 A1    Apr. 17, 2014

Related U.S. Application Data

(60) Provisional application No. 61/493,539, filed on Jun. 6, 2011.

(51) Int. Cl.
*A61M 16/00* (2006.01)
*A61M 16/08* (2006.01)
*A61M 16/06* (2006.01)

(52) U.S. Cl.
CPC .... *A61M 16/0051* (2013.01); *A61M 16/0057* (2013.01); *A61M 16/0066* (2013.01); *A61M 16/0069* (2014.02); *A61M 16/024* (2017.08); *A61M 16/06* (2013.01); *A61M 16/0875* (2013.01); *A61M 16/0009* (2014.02); *A61M 2016/0027* (2013.01); *A61M 2016/0036* (2013.01); *A61M 2016/0039* (2013.01); *A61M 2205/3365* (2013.01);
(Continued)

(58) Field of Classification Search
CPC .......... A61M 16/0051; A61M 16/0057; A61M 16/0069; A61M 16/0066; A61M 2205/52; A61M 2205/3584; A61M 2205/3365; A61M 2016/0036; A61M 2016/0027; A61M 2016/0034; A61M 2230/42; A61M 16/021; A61M 16/022; A61M 16/024; A61M 2205/33; A61M 2205/3327
USPC ...................................................... 128/204.23
See application file for complete search history.

(56) References Cited

U.S. PATENT DOCUMENTS

| 7,890,342 B1 * | 2/2011 | Yruko | G16H 15/00 705/2 |
|---|---|---|---|
| 2005/0080461 A1 | 4/2005 | Stahmann | |
| 2006/0247546 A1 | 11/2006 | Nose | |

(Continued)

FOREIGN PATENT DOCUMENTS

| CN | 101035584 A | 9/2007 |
|---|---|---|
| CN | 101366672 A | 2/2009 |

(Continued)

*Primary Examiner* — Timothy A Stanis
*Assistant Examiner* — Margaret M Luarca (57) ABSTRACT

A respiratory therapy device is configured, such that it switches from one therapy mode to another therapy mode. The mode parameters for the latter therapy mode are based on usage information gather during the former therapy mode.

16 Claims, 5 Drawing Sheets

(52) U.S. Cl.
CPC . *A61M 2205/3584* (2013.01); *A61M 2205/52* (2013.01); *A61M 2230/42* (2013.01)

(56) References Cited

U.S. PATENT DOCUMENTS

| | | | | |
|---|---|---|---|---|
| 2007/0142741 | A1* | 6/2007 | Berthon-Jones | A61B 5/087 600/534 |
| 2007/0193583 | A1* | 8/2007 | Reed | A61M 16/00 128/204.18 |
| 2008/0060647 | A1* | 3/2008 | Messenger | A61M 16/00 128/204.23 |
| 2008/0202528 | A1* | 8/2008 | Carter | A61M 16/0051 128/204.23 |
| 2008/0216832 | A1 | 9/2008 | Carter | |
| 2010/0049008 | A1* | 2/2010 | Doherty | A61B 5/0476 600/301 |
| 2010/0108064 | A1* | 5/2010 | Blackwell | A61M 16/0051 128/204.21 |
| 2011/0100366 | A1* | 5/2011 | Chou | A61B 5/0205 128/204.23 |

FOREIGN PATENT DOCUMENTS

| | | |
|---|---|---|
| CN | 102028997 A | 4/2011 |
| WO | WO2006037184 A1 | 4/2006 |

* cited by examiner

CONFIGURATION OF RESPIRATORY THERAPY MODES

CROSS-REFERENCE TO RELATED APPLICATIONS

This patent application claims the priority benefit under 35 U.S.C § 371 of international patent application no. PCT/IB2012/052798, filed Jun. 4, 2012, which claims the priority benefit under 35 U.S.C. § 119(e) of U.S. Provisional Application No. 61/493,539 filed on Jun. 6, 2011, the contents of which are herein incorporated by reference.

BACKGROUND OF THE INVENTION

1. Field of the Invention

The present disclosure pertains to methods and systems to configure respiratory therapy modes in respiratory therapy devices.

2. Description of the Related Art

Treating respiratory disorders, including sleep apnea, with pressure support therapy is known. In particular, the use of constant positive airway pressure (CPAP) therapy mode is common. Healthcare providers may prescribe a particular therapy mode for a trial period, before deciding on another therapy mode for a longer term.

SUMMARY OF THE INVETNION

One or more embodiments of the present disclosure relate to providing a system to configure respiratory therapy modes for users of respiratory therapy devices. The system comprises a data gathering module and a device configuration module. The data gathering module is configured to receive usage information from respiratory therapy devices, which comprises a first device. The usage information received from the first device represents therapeutic usage of the first device in a first therapy mode. The device configuration module is configured to interact with respiratory devices, such that, responsive to the first device being used in the first therapy mode for a threshold amount of time, the device configuration module transmits a command to the first device that causes the first device to switch from the first therapy mode to a second therapy mode. The command further dictates one or more mode parameters of the second therapy mode that are determined based on the usage information received from the first device while it was operating in the first therapy mode.

It is yet another aspect of one or more embodiments to provide a method for configuring respiratory therapy modes for users of respiratory therapy devices. The method comprises receiving usage information from respiratory therapy devices, wherein the respiratory therapy devices comprise a first device, and wherein the usage information received from the first device represents therapeutic usage of the first device in a first therapy mode; and responsive to the first device being used in the first therapy mode for a threshold amount of time, transmitting a command to the first device that causes the first device to switch from the first therapy mode to a second therapy mode, wherein the command further dictates one or more mode parameters of the second therapy mode for the first device, and wherein the one or more mode parameters are determined based on the usage information received from the first device while the first device was operating in the first therapy mode.

It is yet another aspect of one or more embodiments to provide a system for configuring respiratory therapy modes for users of respiratory therapy devices. The system comprises means for receiving usage information from respiratory therapy devices, wherein the respiratory therapy devices comprise a first device, and wherein the usage information received from the first device represents therapeutic usage of the first device in a first therapy mode; and means for transmitting a command, responsive to the first device being used in the first therapy mode for a threshold amount of time, wherein the command causes the first device to switch from the first therapy mode to a second therapy mode, wherein the command further dictates one or more mode parameters of the second therapy mode for the first device, and wherein the one or more mode parameters are determined based on the usage information received from the first device while the first device was operating in the first therapy mode.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of any limits.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Respiratory therapy devices, or positive airway pressure (PAP) devices, are configured to provide pressurized flows of breathable gas to the airway of a subject to maintain a positive airway pressure of the subject. Such devices may be used to reduce respiratory events (e.g., apneas, hypopneas, Cheyne-Stokes breathing, and/or other events) during sleep. The respiratory therapy devices may be configured locally (using a UI, smart card, and/or other local technique, device, or process, for configuration, or combination thereof), or remotely (using one or more networks, and/or other remote technique, device, or process, for configuration or combination thereof), and/or both. Configuration may be under control of (automated) programming (e.g. internal to a respiratory therapy device), or may be under control of a care provider, and/or a combination of both.

A device may connect to a server to facilitate the exchange of information, including commands that cause the device to switch from a first therapy mode to a second therapy mode. A "mode" of a respiratory therapy device broadly defines the range of capabilities, pertaining to inhalation pressure levels and exhalation pressure levels, that a respiratory therapy device can perform. Examples of therapy modes may include one or more of a CPAP mode, a multi-pressure (e.g., bi-level) mode, a volume-control mode, and/or other modes. Some therapy modes are capable of auto-titration (e.g. Auto-CPAP, CFlex, A-Flex, Auto-Bi-level, etc.), whereas other modes are not. The commands may further dictate one or more mode parameters for a therapy mode of the device. Mode parameters may affect the operation of a respiratory therapy device in a particular therapy mode in a persistent manner, i.e. for more than one respiratory cycle. Examples of mode parameters are a constant pressure level, an inspiratory pressure level (IPAP), an expiratory pressure level (EPAP), maximum pressures, minimum pressures, the differences between IPAP and EPAP, rate of change of pressure, the shape or waveform followed between pressure transitions, backup breath rates, and/or other parameters that affect the operation of a respiratory device whilst in a particular therapy mode.

For example, a care provider may determine through a diagnostic analysis that a particular pressure level (of CPAP) is likely suitable for a given subject. One way to verify whether this particular pressure level is suitable (e.g. comfortable and/or effective) may be to configure the respiratory therapy device associated with the given subject to initiate a trial therapy mode for a trial period. The trial period could range from 1 to 30 (calendar and/or usage) days. The trial therapy mode of the device may be a mode in which pressure and/or flow of the pressurized flow of breathable gas generated by the device are adjusted on a relatively ongoing manner (e.g., each breath, every few breaths, every few seconds, etc.) during an individual therapy session to titrate the therapy. For example, the trial therapy mode may be an auto-titrating CPAP mode.

Throughout the trial period, therapeutic usage information may be gathered (either by the device, by a server that the device can connect to, and/or by a combination of both). Based on the gathered usage information, a mode parameter, such as, for example, a pressure level (e.g., a "90% pressure", and/or other parameters) may be determined (either by the device, by a server that the device can connect to, and/or by a combination of both) for a subsequent mode of respiratory therapy. At the end of the trial period (or at another opportune moment), one or more commands may cause the device to switch from the trial therapy mode to a second therapy mode. The commands may be transmitted to the device by a server that the device can connect to, or may originate from a care provider, or may be under control of (automated) programming (e.g. internal to the device), and/or some combination thereof. The commands may further dictate one or more mode parameters of the second therapy mode based on the gathered usage information, such as the recommended constant pressure level to be used in the CPAP therapy mode.

Figure 1:
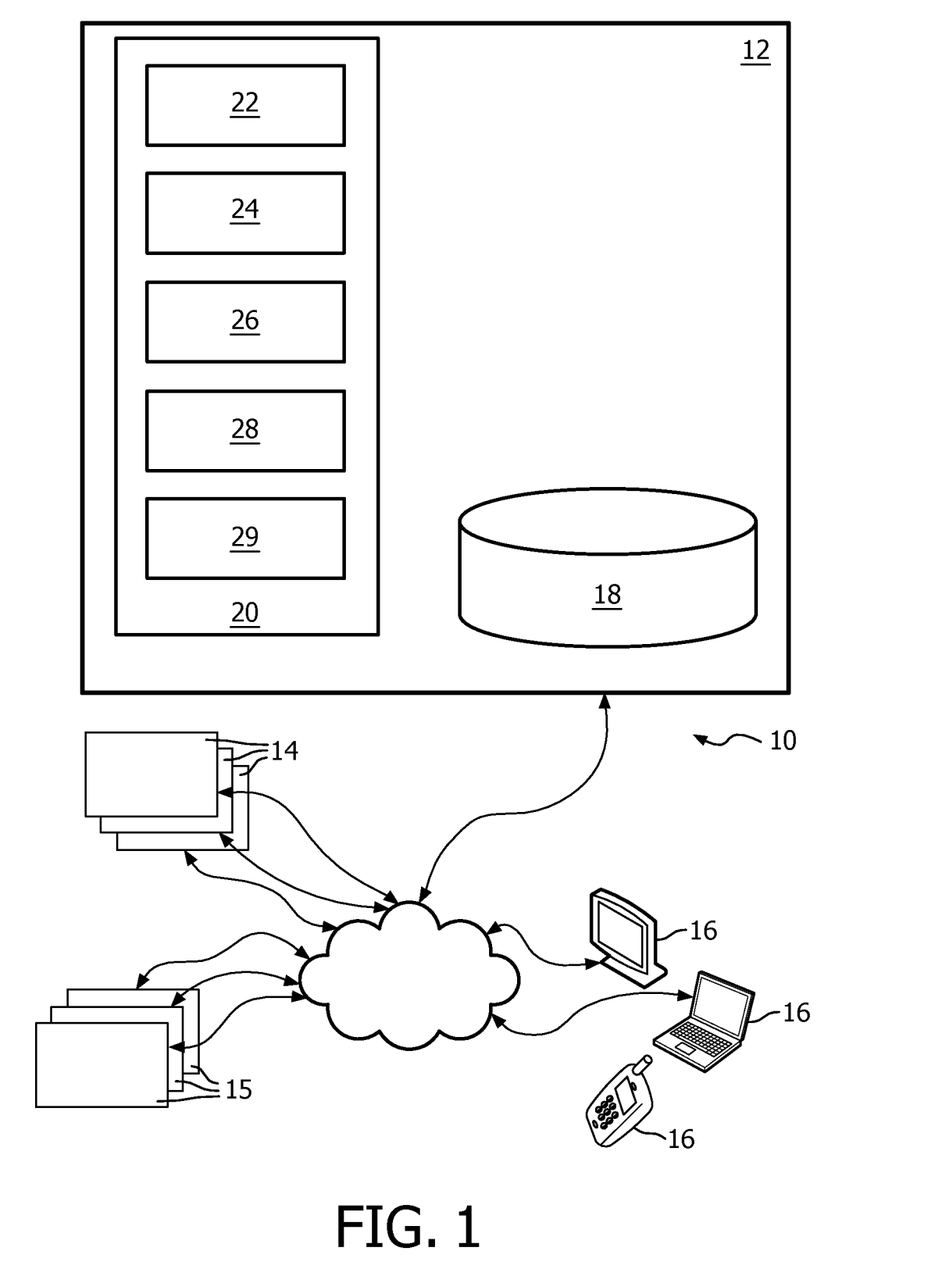
FIG. 1 schematically illustrates a system to configure respiratory therapy modes for users of respiratory therapy devices.

FIG. 1 schematically illustrates a system 10 to configure respiratory therapy modes for users of respiratory therapy devices 14. System 10 may include one or more servers 12, and/or other components. System 10 may operate in communication and/or coordination with one or more external sources 15, and respiratory therapy devices 14. System 10 may operate remotely from respiratory therapy devices 14, or any part of the functionality described herein as attributed to system 10 may be implemented as part of the respiratory therapy devices 14. Users, including care providers, may interface with system 10 and/or respiratory therapy devices 14 via client computing platforms 16.

The components of system 10, servers 12, respiratory therapy devices 14, and/or client computing platforms 16 may be operatively linked via one or more electronic communication links. For example, such electronic communication links may be established, at least in part, via one or more networks such as the Internet and/or other networks. It will be appreciated that this is not intended to be limiting, and that the scope of this disclosure includes implementations in which servers 12, respiratory therapy devices 14, and/or client computing platforms 16 may be operatively linked via some other communication media. The components of system 10 may be integrated into fewer or more devices than shown in FIG. 1. The described functionality of the components of system 10 may be distributed across partitions different from the one shown in FIG. 1. For example, the user interface for a care provider may be integrated into a respiratory therapy device.

As is discussed further below with respect to FIG. 2, respiratory therapy devices 14 are capable of configuration in accordance with one or more embodiments. A given respiratory therapy device 14 is configured to provide respiratory therapy through the supply of a pressurized flow of breathable gas to a subject in accordance with a therapeutic respiratory regimen.

A given client computing platform 16 may include one or more processors configured to execute computer program modules. The computer program modules may be configured to enable one or more users (e.g. care providers) associated with the given client computing platform 16 to interface with system 10 and/or respiratory therapy devices 14, and/or provide other functionality attributed herein to client computing platforms 16. By way of non-limiting example, the given client computing platform 16 may include one or more of a desktop computer, a laptop computer, a handheld computer, a NetBook, a Smartphone, a gaming console, and/or other computing platforms. Alternatively, and/or simultaneously, a given client computing platform 16 may be integrated in or embedded in a user's respiratory therapy device 14.

External resources 15 may include sources of information, external entities participating with system 10, therapeutic devices, and/or other resources. In some implementations, some or all of the functionality attributed herein to external resources 15 may be provided by resources included in system 10.

Server 12 may configure, or cooperate with client computing platforms 16 to configure, one or more respiratory therapy modes for users of respiratory therapy devices 14. Server 12 may include electronic storage 18, one or more processors 20, and/or other components. Server 12 may include communication lines, or ports to enable the exchange of information with a network and/or other computing platforms.

Electronic storage 18 may comprise electronic storage media that electronically stores information. The electronic storage media of electronic storage 18 may include one or both of system storage that is provided integrally (i.e., substantially non-removable) with server 12 and/or removable storage that is removably connectable to server 12 via, for example, a port (e.g., a USB port, a FireWire port, etc.) or a drive (e.g., a disk drive, etc.). Electronic storage 18 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 18 may store software algorithms, information determined by processor 20, information obtained, identified, gathered, and/or provided by one or more computer program modules, information received from server 12, information received from client computing platforms 16, information received from respiratory therapy devices 14, and/or other information that enables server 12 to function properly.

Processor(s) 20 is configured to provide information processing capabilities in server 12. As such, processor 20 may include one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may include a plurality of processing units. These processing units may be physically located within the same device, or processor 20 may represent processing functionality of a plurality of devices operating in coordination.

As is shown in FIG. 1, processor 20 may be configured to execute one or more computer program modules. The one or more computer program modules may include one or more of a data gathering module 22, a device configuration module 24, a timing module 26, a mode parameter module 28, an analysis module 29, and/or other modules. Processor 20 may be configured to execute modules 22, 24, 26, 28, and/or 29 by software; hardware; firmware; some combination of software, hardware, and/or firmware; and/or other mechanisms for configuring processing capabilities on processor 20.

It should be appreciated that although modules 22, 24, 26, 28, and 29 are illustrated in FIG. 1 as being co-located within a single processing unit, in implementations in which processor 20 includes multiple processing units, one or more of modules 22, 24, 26, 28, and/or 29 may be located remotely from the other modules. The description of the functionality provided by the different modules 22, 24, 26, 28, and/or 29 described below is for illustrative purposes, and is not intended to be limiting, as any of modules 22, 24, 26, 28, and/or 29 may provide more or less functionality than is described. For example, one or more of modules 22, 24, 26, 28, and/or 29 may be eliminated, and some or all of its functionality may be provided by other ones of modules 22, 24, 26, 28, and/or 29. As another example, processor 20 may be configured to execute one or more additional modules that may perform some or all of the functionality attributed below to one of modules 22, 24, 26, 28, and/or 29.

It will be appreciated that the illustration of modules 22, 24, 26, 28, and/or 29 being executed solely on processor 20 separate from client computing platforms 16 and respiratory therapy devices 14 is not intended to be limiting. For example, in some implementations, the client computing platforms 16 may be configured to provide locally at least some of the functionality attributed above to one or more of modules 22, 24, 26, 28, and/or 29. Similarly, one or more of modules 22, 24, 26, 28, and/or 29 may be executed locally on individual client computing platforms 16 while others are executed on server 12. As another example, in some implementations, the respiratory therapy devices 14 may be configured to provide locally at least some of the functionality attributed above to one or more of modules 22, 24, 26, 28, and/or 29. Similarly, one or more of modules 22, 24, 26, 28, and/or 29 may be executed locally on individual respiratory therapy devices 14 while others, if present, may be executed remotely from individual respiratory therapy devices 14.

Data gathering module 22 is configured to receive usage information from respiratory therapy devices 14. The usage information received from a given respiratory therapy device represents therapeutic usage of the given device in its current therapy mode. For example, a given respiratory therapy device may operate in a CPAP therapy mode and transmit daily usage information. The usage information may include the total hours of cumulative therapeutic usage during the previous 24 hours. Usage information may be associated with either a particular respiratory therapy device, a particular user, or both. Usage information may include one or more of a therapy starting date, user experience level, an average duration of daily usage, total (cumulative) hours of usage, a usage pattern, metrics indicating quality of therapy and/or quality of sleep, level of compliance with a therapy regimen, therapeutic device characteristics (e.g. mask type or PAP device settings), derived usage characteristics, user-stated usage characteristics, and/or other usage information.

User-stated usage characteristics may include issues or problems the user is experiencing while undergoing therapy, and/or other user-stated usage characteristics. Derived usage characteristics may include low and/or irregular usage (as detected e.g. through analysis of usage reports), decreasing usage, excessive mask leak, and/or other derived usage characteristics. A device used by a subject may (autonomously and/or periodically) compile a usage report and submit it to server 12, data gathering module 22, and/or any other constituent component of system 10.

Timing module 26 may be configured to determine whether a threshold amount of therapeutic usage time has elapsed for an individual respiratory therapy device 14. For a given device, a threshold amount of time may include one or both of a cumulative usage threshold and/or a consecutive usage threshold. For example, system 10 may be configured to switch from a default or trial therapy mode to another therapy mode only after at least twelve total hours of therapeutic usage have occurred, and/or at least four hours of consecutive therapeutic usage have occurred. Alternatively, and/or simultaneously, timing module 26 may be configured to determine whether a trial period for a trial mode has expired. A trial period may be specified in calendar days, usage hours and/or usage days. Operation of constituent components of system 10, e.g. device configuration module 24, may be performed responsive to a determination by timing module 26. Determinations by timing module 26 may be used in other components of system 10, such as data gathering module 22, e.g. to determine a switch condition. Some or all of the functionality attributed herein to timing module 26 may be performed locally in an individual respiratory therapy device 14.

Mode parameter module 28 may be configured to determine parameters of a therapy mode, including, but not limited to, a pressure level. Operation of mode parameter module 28 may be based on usage information received by data gathering module 22. For example, mode parameter module 28 may provide a recommended (constant) pressure level to be included in a command that causes the device to switch therapy modes. A determined mode parameter may be a pressure statistic, such as the pressure level below which 90% of (part of) a trial period is spent. Mode parameter module 28 may be configured to automatically update parameters of a current therapy mode based on information gathered during therapeutic usage of the current therapy mode. Determinations by mode parameter module 28 may be used in other modules, such as device configuration module 24, e.g. as part of (transmitted) commands.

Device configuration module 24 is configured to interact with respiratory therapy devices 14 to adjust operation of respiratory therapy devices 14. This includes adjusting one or more of a mode of operation, one or more parameters of a mode of operation, and/or other aspects/features of the operation of a respiratory therapy device. In some embodiments, responsive to a given respiratory therapy device being used in its current therapy mode for at least a threshold amount of time, device configuration module 24 commands the given device to switch from its current therapy mode to another therapy mode. This may be referred to as activating another therapy mode. Device configuration module 24 may transmit a command (e.g. if device configuration module 24 is located remotely from the given respiratory therapy device 14) that causes the given device to switch therapy modes. Alternatively, or simultaneously, device configuration module 24 may issue the command (e.g. if device configuration mode 24 is located locally within the given respiratory therapy device 14) that causes the given device to switch therapy modes. System 10 may determine one or more mode parameters for the newly activated therapy mode based on usage information received by data gathering module 22. The (transmitted) command may further dictate one or more determined mode parameters of the newly activated therapy mode for the given device.

Device configuration module 24 may be configured such that a (transmitted) command further specifies a switch condition that causes the device to switch from the newly activated therapy mode back to the initial or default therapy mode (e.g. auto-titrating CPAP). The switch condition may e.g. depend on usage information, and/or other information.

Analysis module 29 may be configured to determine an index or measure related to the effectiveness and/or efficiency of the therapy provided by respiratory therapy device 14, based on the received usage information. Such indexes or measures may include a respiratory disturbance index (RDI), an apnea-hypopnea-index (AHI), a snore index, a sleep quality index, and/or other indexes or information related to the effectiveness and/or efficiency of the therapy provided by respiratory therapy device 14. The RDI may be determined by adding together the number of apneas, the number of hypopneas, and the number of respiratory effort related arousals (RERAs) in a given time period. RDI may be interpreted as a measure for the effectiveness of a particular respiratory therapy. For example, analysis module 29 may be configured to determine (autonomously, without explicit intervention from a care provider and/or a user) that a current therapy mode is not sufficiently effective. Responsive to such a determination, system 10 may be configured to issue and/or transmit commands to a respiratory therapy device that change its operating parameters and/or mode.

Figure 2:
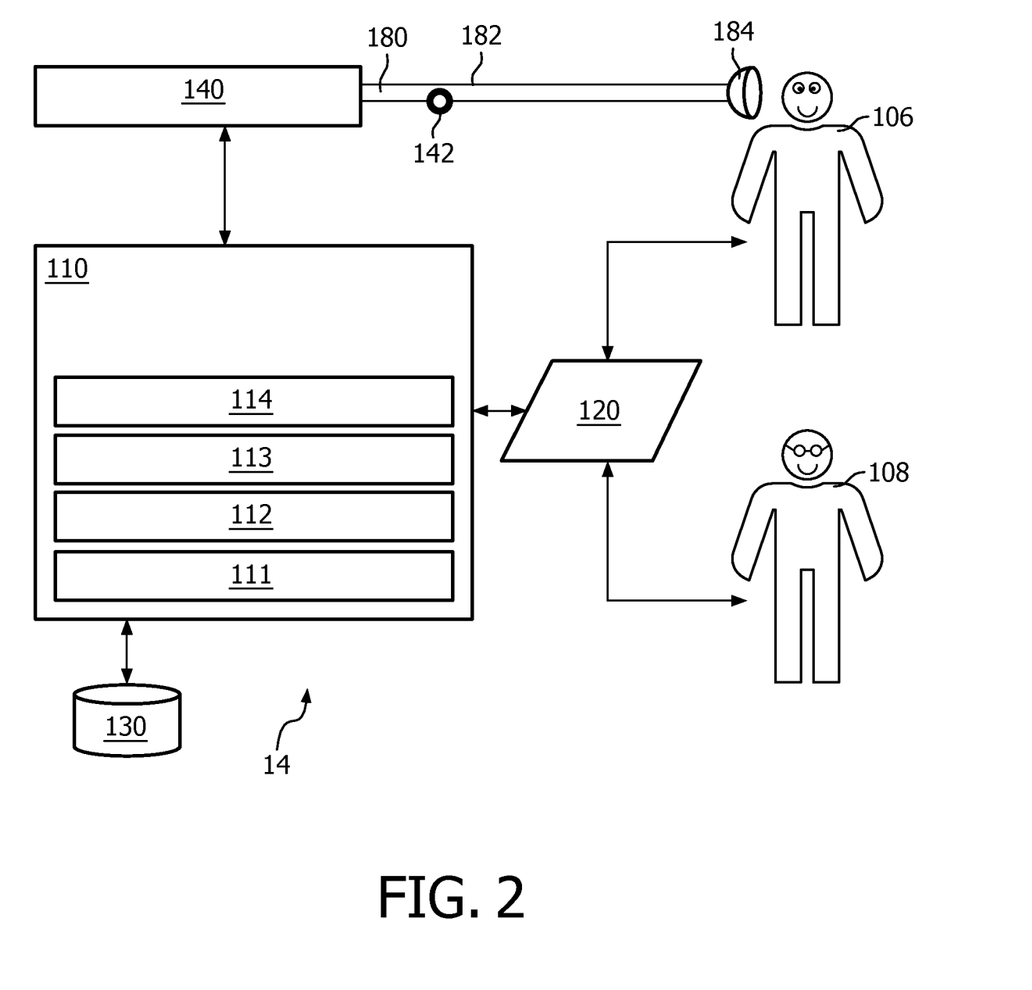
FIG. 2 schematically illustrates a respiratory therapy device capable of configuration in accordance with one or more embodiments.

FIG. 2 schematically illustrates a respiratory therapy device 14 that is capable of configuration in accordance with one or more embodiments. Respiratory therapy device 14 may comprise one or more of a pressure generator 140, a processor 110, a sensor 142, an electronic storage 130, a user interface 120, a subject interface 180, and/or other constituent components.

Pressure generator 140 is configured to provide a pressurized flow of breathable gas to the airway of subject 106, e.g. via subject interface 180. Subject 106 may or may not initiate one or more phases of respiration. Pressure support may be implemented as a higher and lower positive pressure of a (multi-level) PAP device. For example, to support inspiration, the pressure of the pressurized flow of breathable gas is adjusted to an Inspiratory Positive Air Pressure (IPAP). Similarly, to support expiration, the pressure of the pressurized flow of breathable gas is adjusted to an Expiratory Positive Air Pressure (EPAP). Other schemes for providing respiratory support through the delivery of the pressurized flow of breathable gas are contemplated. Note that a pressure level need not be constant throughout an entire phase of respiration.

Respiratory therapy device 14 may be configured such that one or more gas parameters of the pressurized flow of breathable gas are controlled in accordance with a therapeutic respiratory regimen for subject 106. The one or more gas parameters include one or more of flow, volume, retrograde volume, pressure, humidity, velocity, acceleration, (intentional) gas leak, and/or other parameters. Respiratory therapy device 14 may be configured to provide types of therapy including types of therapy where a subject performs inspiration and/or expiration of his own accord or where the device provides negative airway pressure.

A therapy "session" of using a respiratory therapy device 14 may be defined as a period of consecutive therapeutic usage of the respiratory therapy device, not to exceed 24 consecutive hours. If the respiratory therapy is used to treat sleeping disorders, such as sleep apnea, the related session length may correspond to the sleeping pattern of a subject. A typical session length may thus be 6-8 hours. In some modes of respiratory therapy, one or more pressure levels are adjusted on a relatively ongoing manner (e.g., each breath, every few breaths, every few seconds, etc.) during an individual therapy session to titrate the therapy. In other modes of therapy, adjustments may be made only between sessions rather than during sessions.

A pressurized flow of breathable gas is delivered from pressure generator 140 to or near the airway of subject 106 by a subject interface 180. Subject interface 180 includes a conduit 182, a subject interface appliance 184, and/or other components. Conduit 182 may be a flexible length of hose, or other conduit, that places subject interface appliance 184 in fluid communication with pressure generator 140. Conduit 182 forms a flow path through which the pressurized flow of breathable gas is communicated between subject interface appliance 184 and pressure generator 140.

Subject interface appliance 184 is configured to deliver the pressurized flow of breathable gas to the airway of subject 106. As such, subject interface appliance 184 may include any appliance suitable for this function. In certain embodiments, pressure generator 140 is a dedicated ventilation device and subject interface appliance 184 is configured to be removably coupled with another interface appliance being used to deliver respiratory therapy to subject 106. For example, subject interface appliance 184 is configured to engage with and/or be inserted into an endotracheal tube, a tracheotomy portal, and/or other interface appliances. In certain embodiments, subject interface appliance 184 is configured to engage the airway of subject 106 without an intervening appliance. In this embodiment, subject interface appliance 184 includes one or more of an endotracheal tube, a nasal cannula, a tracheotomy tube, a nasal mask, a nasal/oral mask, a full face mask, a total face mask, a partial rebreathing mask, or other interface appliances that communicate a flow of gas with an airway of a subject. The present disclosure is not limited to these examples, and contemplates delivery of the pressurized flow of breathable gas to subject 106 using any subject interface.

Respiratory therapy device 14 may include electronic storage 130 comprising electronic storage media that electronically stores information. The electronic storage media of electronic storage 130 includes one or both of system storage that is provided integrally (i.e., substantially non-removable) with respiratory therapy device 14 and/or removable storage that is removably connectable to respiratory therapy device 14 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media.

Electronic storage 130 stores software algorithms, information determined by processor 110, information received via user interface 120, and/or other information that enables respiratory therapy device 14 to function properly. For example, electronic storage 130 may record or store timing information (including duration of inhalation phases and exhalation phases as well as transitional moments), one or more (breathing) parameters and/or other parameters (as discussed elsewhere herein), pressure levels, information indicating whether the subject adequately complied with a prescribed respiratory therapy regimen, information indicating whether a respiratory event (including Cheyne-Stokes respiration, central sleep apnea, obstructive sleep apnea, hypopnea, snoring, hyperventilation, and/or other respiratory events) occurred, and/or other information. Electronic storage 130 may be a separate component within respiratory therapy device 14, or electronic storage 130 may be provided integrally with one or more other components of respiratory therapy device 14 (e.g., processor 110).

Respiratory therapy device 14 may include user interface 120 configured to provide an interface between respiratory therapy device 14 and a user (e.g., user 108, subject 106, a caregiver, a therapy decision-maker, etc.) through which the user can provide information to and receive information from respiratory therapy device 14. This enables data, results, and/or instructions and any other communicable items, collectively referred to as "information," to be communicated between the user and respiratory therapy device 14. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information is e.g. provided to subject 106 by user interface 120 in the form of auditory signals, visual signals, tactile signals, and/or other sensory signals.

By way of non-limiting example, in certain embodiments, user interface 120 includes a radiation source capable of emitting light. The radiation source includes one or more of an LED, a light bulb, a display screen, and/or other sources. User interface 120 controls the radiation source to emit light in a manner that conveys to subject 106 information related to breathing and/or the pressurized flow of breathable gas. Note that the subject and the user of respiratory therapy device 14 may be the same person.

It is to be understood that other communication techniques, either hard-wired or wireless, are also contemplated herein as user interface 120. For example, in one embodiment, user interface 120 is integrated with a removable storage interface provided by electronic storage 130. In this example, information is loaded into respiratory therapy device 14 from removable storage (e.g., a smart card, a flash drive, a removable disk, etc.) that enables the user(s) to customize the implementation of respiratory therapy device 14. Other exemplary input devices and techniques adapted for use with respiratory therapy device 14 as user interface 120 include, but are not limited to, an RS-232 port, RF link, an IR link, modem (telephone, cable, Ethernet, internet or other). In short, any technique for communicating information with respiratory therapy device 14 is contemplated as user interface 120.

Respiratory therapy device 14 may include sensor 142 configured to generate one or more output signals conveying measurements related to respiratory parameters, including one or more of flow, pressure, humidity, velocity, acceleration, and/or other respiratory parameters. Output signals may convey measurements related to respiratory parameters. Based on these respiratory parameter, respiratory therapy device 14 (and/or any constituent components thereof) may be configured to determine one or more breathing parameters, including (tidal) volume, retrograde volume, respiratory rate, breathing period, inhalation time or period, exhalation time or period, peak flow, flow rate, respiration flow curve shape, transition time from inhalation to exhalation and/or vice versa, transition time from peak inhalation flow rate to peak exhalation flow rate and/or vice versa, respiration pressure curve shape, (intentional) gas leak, and/or other breathing parameters. Sensor 142 may be in fluid communication with conduit 182 and/or subject interface appliance 184.

The illustration of sensor 142 as including a single member in FIG. 2 is not intended to be limiting. In certain embodiments sensor 142 includes a plurality of sensors operating as described above by generating output signals conveying information related to parameters associated with the gas breathed by subject 106 and/or the delivery of the gas to subject 106. For example, a breathing parameter may be related to a mechanical unit of measurement of a component of respiratory therapy device 14 such as rotor speed, motor speed, blower speed, fan speed, or a related measurement that serves as a proxy for any of the previously listed breathing parameters through a previously known/calibrated mathematical relationship. Resulting signals or information from sensor 142 may be transmitted to processor 110, user interface 120, electronic storage 130, and/or other components of respiratory therapy device 14. This transmission can be wired and/or wireless.

Processor 110 is configured to provide information processing capabilities in respiratory therapy device 14. As such, processor 110 includes one or more of a digital processor, an analog processor, a digital circuit designed to process information, an analog circuit designed to process information, a state machine, and/or other mechanisms for electronically processing information. Although processor 110 is shown in FIG. 2 as a single entity, this is for illustrative purposes only. In some implementations, processor 110 includes a plurality of processing units.

As is shown in FIG. 2, processor 110 is configured to execute one or more computer program modules. The one or more computer program modules include one or more of a control module 111, a usage module 112, a configuration module 113, a connectivity module 114, and/or other modules. Processor 110 may be configured to execute modules 111, 112, 113, and/or 114 by software; hardware; firmware; some combination of software, hardware, and/or firmware; and/or other mechanisms for configuring processing capabilities on processor 110.

It should be appreciated that although modules 111, 112, 113, and 114 are illustrated in FIG. 2 as being co-located within a single processing unit, in implementations in which processor 110 includes multiple processing units, one or more of modules 111, 112, 113, and/or 114 may be located remotely from the other modules. The description of the functionality provided by the different modules 111, 112, 113, and/or 114 described below is for illustrative purposes, and is not intended to be limiting, as any of modules 111, 112, 113, and/or 114 may provide more or less functionality than is described. For example, one or more of modules 111, 112, 113, and/or 114 may be eliminated, and some or all of its functionality may be provided by other ones of modules 111, 112, 113, and/or 114. Note that processor 110 may be configured to execute one or more additional modules that may perform some or all of the functionality attributed below to one of modules 111, 112, 113, and/or 114.

Control module 111 is configured to control pressure generator 140 in the provision of adjusting pressure levels for respiratory therapy device 14, to provide the pressurized flow of breathable gas at inhalation pressure levels during inhalation phases, and at exhalation pressure levels during exhalation phases. In some modes of operation, inhalation pressure levels may be the same as exhalation pressure levels.

Usage module 112 is configured to monitor, track, and/or gather therapeutic usage information for a given user associated with the respiratory therapy device 14, i.e. a respiratory therapy device. Usage information may include one or more of a therapy starting date, user experience level, an average duration of daily usage, a usage pattern, metrics indicating quality of therapy and/or quality of sleep, level of compliance with a therapy regimen, therapeutic device characteristics (e.g. mask type or operational settings), derived usage characteristics, user-stated usage characteristics, and/or other usage information. User-stated usage characteristics may include issues or problems the user is experiencing while undergoing therapy, and/or other user-stated usage characteristics. Derived usage characteristics may include low and/or irregular usage (as detected e.g. through analysis of usage reports), decreasing usage, excessive mask leak, and/or other derived usage characteristics.

Configuration module 113 is configured to adjust mode settings and other operational parameters for respiratory therapy device 14. For example, configuration module 113 may have one set of operational parameters for a first therapy mode, and a second set of operational parameters for a second therapy mode. The first therapy mode may be an initial or default therapy mode. For example, a new user (e.g. newly registered user of system 10) using respiratory therapy device 14 may start respiratory therapy by default in a particular therapy mode, such as an auto-titrating CPAP therapy mode.

Connectivity module 114 is configured to enable interaction between respiratory therapy device 14 and system 10. Connectivity module 114 may transmit information, such as usage information from usage module 112, to system 10 (and/or data gathering module 22 shown in FIG. 1). Connectivity module 114 may receive commands transmitted by system 10 (and/or device configuration module 24 shown in FIG. 1). For example, such a command may contain instructions to change a mode parameter. Connectivity module 114 may cause configuration module 113 to carry out the instructions contained in the command.

Figure 3:
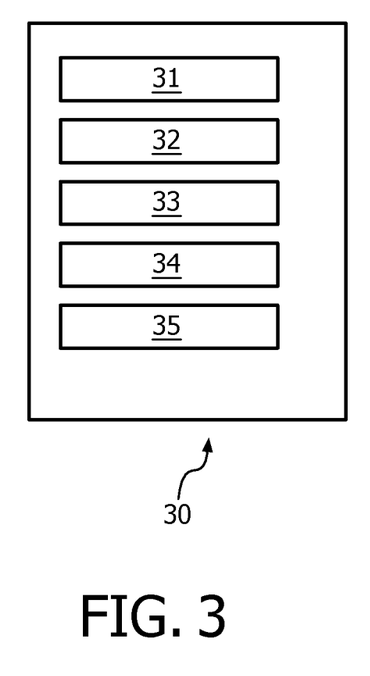
FIG. 3 illustrates an exemplary embodiment of a user interface within a respiratory therapy device capable of configuration in accordance with one or more embodiments.

FIG. 3 illustrates an exemplary embodiment of a user interface 30 within a respiratory therapy device, i.e. respiratory therapy device 14, capable of configuration in accordance with one or more embodiments described herein. User interface 30 may include one or more fields configured to receive entry and/or selection of information pertaining to operational parameters and/or conditions of external resource 14. Field 31 may be a mode field configured to present the current therapy mode to a user. Field 32 may be a parameter field configured to present a current operational parameter pertaining to the current therapy mode. For example, field 32 may present the current pressure level for a current therapy mode. Field 33 may be a timing field configured to present information to a user. For example, if respiratory therapy device 14 is operating in a trial therapy mode, field 33 may present the duration of the trial period, the remaining duration of the trial period, and/or the amount of therapeutic usage in the trial period (e.g. in calendar days or accumulative usage days).

As another example, if respiratory therapy device 14 is operating in a CPAP therapy mode using automatic updating/adjusting of one or more mode parameters, field 33 may present a timer counting down to the next automatic adjustment. Field 34 may be configured to present information to a user, e.g., pertaining to another field such as field 33. For example, field 34 may present the operational pressure level bounds for external resource 14, such as a minimum pressure level and/or a maximum pressure level. Field 35 may be a usage field configured to present usage information to a user. For example, field 35 may present a respiratory disturbance index.

Figure 4:
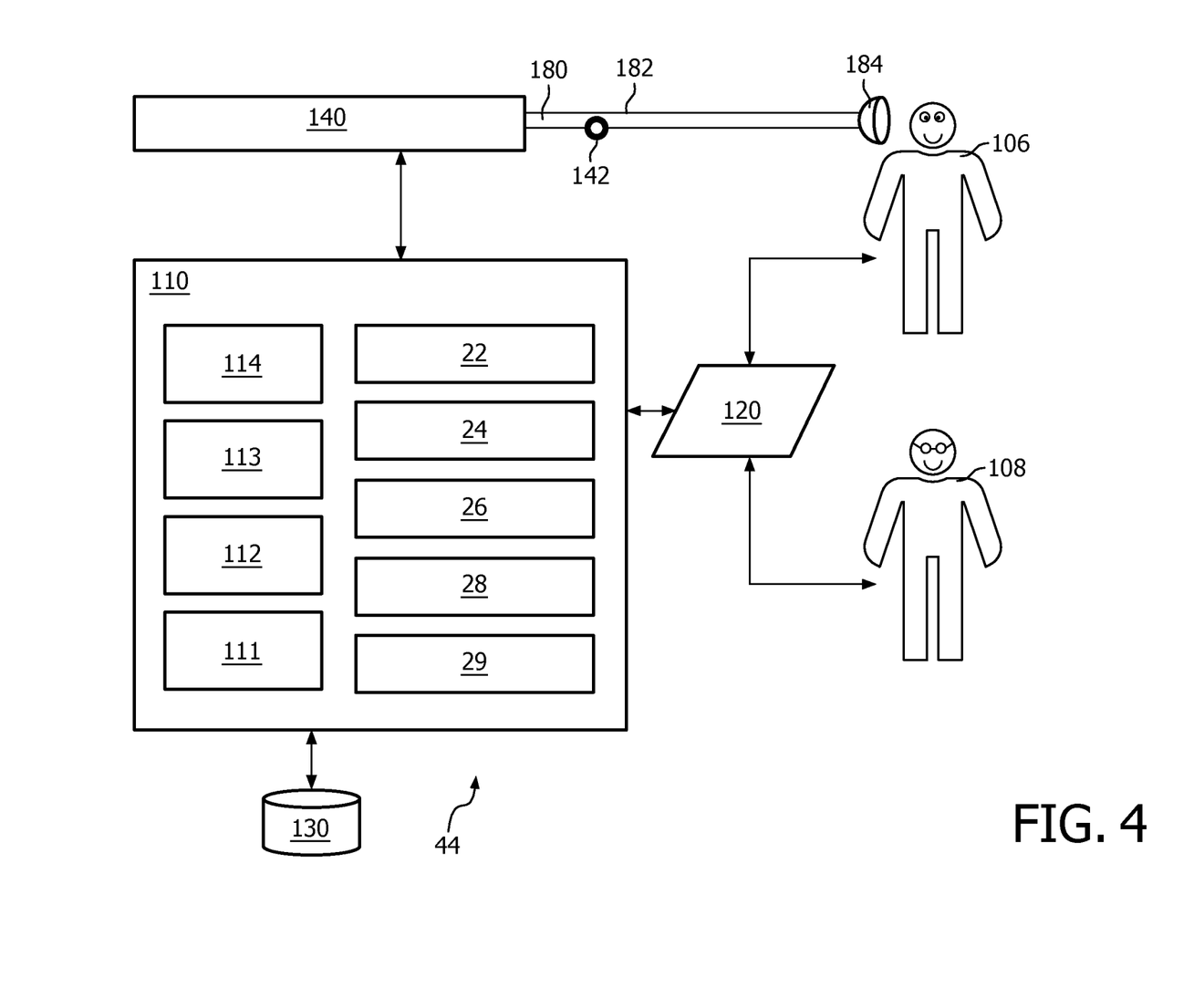
FIG. 4 schematically illustrates a respiratory therapy device capable of configuration in accordance with one or more embodiments.

FIG. 4 schematically illustrates a respiratory therapy device 44 that is capable of configuration in accordance with one or more embodiments. Respiratory therapy device 44 may comprise one or more of pressure generator 140, processor 110, sensor 142, electronic storage 130, user interface 120, subject interface 180, and/or other constituent components. Pressure generator 140, processor 110, sensor 142, electronic storage 130, user interface 120, and subject interface 180 perform the same or similar functionality as their respective counterparts in FIG. 2, described above. Respiratory therapy device 44 includes one or more of control module 111, usage module 112, configuration module 113, and/or connectivity module 114, which perform the same or similar functionality as their respective counterparts in FIG. 2, described above. Respiratory therapy device 44 may further include one or more of data gathering module 22, device configuration module 24, timing module 26, mode parameter module 28, and/or analysis module 29, which perform the same or similar functionality as their respective counterparts in FIG. 1, described above. Respiratory therapy device 44 does not require a connection to one or more networks to perform the functionality of configuring therapy modes.

Figure 5:
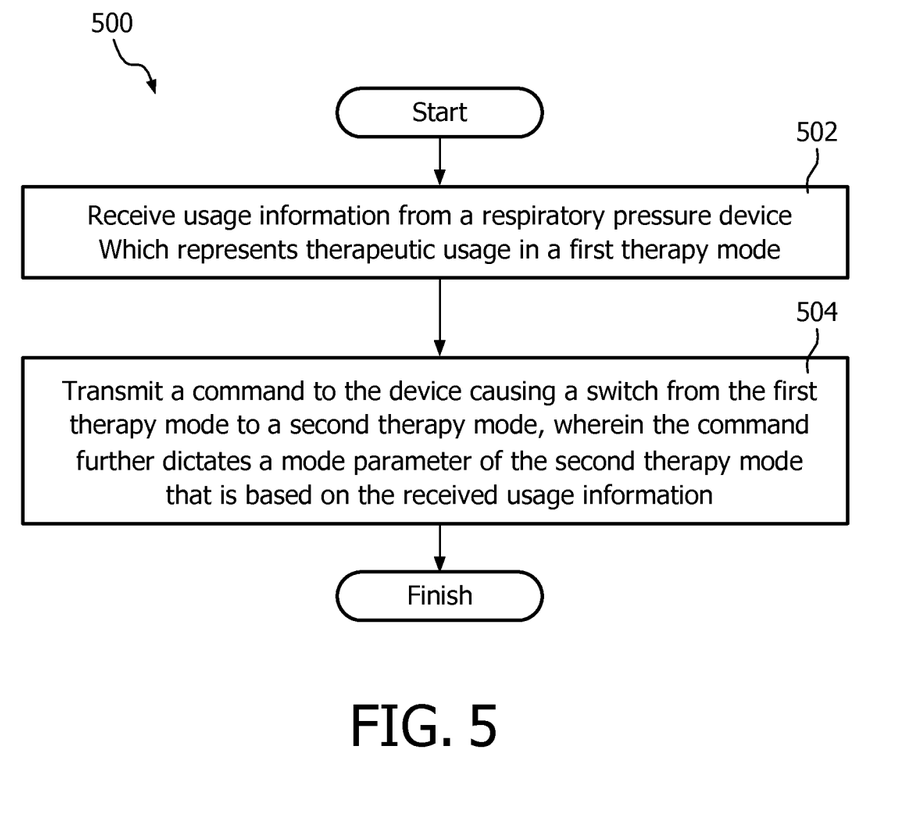
FIG. 5 illustrates a method for configuring respiratory therapy modes for users of respiratory therapy devices.

FIG. 5 illustrates a method 500 of configuring respiratory therapy modes for users of respiratory therapy devices. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, usage information is received from a respiratory therapy device, wherein the usage information represents therapeutic usage of the device in a first therapy mode. In some implementations, operation 502 may be performed by a data gathering module similar to or substantially the same as data gathering module 22 (shown in FIG. 1 and described above).

At an operation 504, a command is transmitted to the respiratory therapy device. The command causes the device to switch from a first therapy mode to a second therapy mode. The command further dictates one or more mode parameters of the second therapy mode that is based on the usage information received during the first therapy mode. In some implementations, operation 504 may be performed by a device configuration module similar to or substantially the same as device configuration module 24 (shown in FIG. 1 and described above).

The present invention also contemplates that the selection of the second therapy mode may be determined based on upon the information gathered during the first therapy mode. For example, the device may operate as an Auto CPAP for the first therapy mode and collect certain information, such as device useage (compliance), time at a certain pressure, frequency/number of respiratory events, such as snoring, apneas, hypopneas, etc. The second mode, as well as one or more of the operating parameters for that mode may be determined based on the information collected. For example, the system may decide between operating as a CPAP or a bi-level device for the second mode, based on the information gathered in the first mode.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the embodiments have been described in detail for the purpose of illustration based on what is currently considered to be most practical and preferred, it is to be understood that such detail is solely for that purpose and that the disclosure is not limited to these embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system to configure respiratory therapy modes for users of a respiratory therapy device, the system comprising:
one or more processors configured to execute computer program modules, the computer program modules comprising:
a data gathering module configured to receive usage information from a respiratory therapy device, wherein the usage information received from the respiratory therapy device includes:
a cumulative therapeutic usage time corresponding to a total amount of time the therapy device is used in a first therapy mode,
a successive therapeutic usage time corresponding to an uninterrupted amount of time the therapy device is used in the first therapy mode, and
a quality of sleep index indicating effectiveness of the first therapy mode during the successive therapeutic usage time;
a timing module configured to determine a first cumulative therapeutic usage threshold amount of time and a second successive therapeutic usage threshold amount of time; and
a device configuration module configured to interact with the respiratory therapy device, wherein the device configuration module is further configured such that responsive to the respiratory therapy device being used in the first therapy mode for at least the first cumulative therapeutic usage threshold amount of time, and the respiratory therapy device being used in the first therapy mode for at least the second successive therapeutic usage threshold amount of time, the device configuration module transmits a command to the respiratory therapy device that causes the respiratory therapy device to switch from the first therapy mode to a second therapy mode, wherein the command further dictates one or more mode parameters of the second therapy mode for the respiratory therapy device, and wherein the one or more mode parameters are determined based on the quality sleep index and the effectiveness of the first therapy mode.

2. The system of claim 1, wherein the command further specifies a switch condition that causes the respiratory therapy device to switch from the second therapy mode to the first therapy mode.

3. The system of claim 1, wherein mode parameters of the second therapy mode are automatically updated based on usage information gathered during therapeutic usage of the second therapy mode.

4. The system of claim 1, wherein the usage information received from the respiratory therapy device further represents a respiratory disturbance index, and wherein the or more mode parameters of the second therapy mode are further determined based on the respiratory disturbance index.

5. The system of claim 1, wherein the one or more mode parameters include a pressure statistic.

6. The system of claim 1, wherein the first therapy mode comprises a CPAP mode, and wherein the second therapy mode comprises a volume control mode, the second therapy mode being different from the first therapy mode.

7. A method for configuring respiratory therapy modes for users of respiratory therapy devices, the method comprising:
   receiving usage information from a respiratory therapy device, wherein the usage information received from the respiratory therapy device includes:
      a cumulative therapeutic usage time corresponding to a total amount of time the therapy device is used in a first therapy mode,
      a successive therapeutic usage time corresponding to an uninterrupted amount of time the therapy device is used in the first therapy mode, and
      a quality of sleep index indicating effectiveness of the first therapy mode during the successive therapeutic usage time;
   determining a first cumulative therapeutic usage threshold amount of time and a second successive therapeutic usage threshold amount of time; and
   responsive to the respiratory therapy device being used in the first therapy mode for at least the first cumulative therapeutic usage threshold amount of time, and the respiratory therapy device being used in the first therapy mode for at least the second successive therapeutic usage threshold amount of time, transmitting a command to the respiratory therapy device that causes the respiratory therapy device to switch from the first therapy mode to a second therapy mode, wherein the command further dictates one or more mode parameters of the second therapy mode for the respiratory therapy device, and wherein the one or more mode parameters are determined based on the quality of sleep index and the effectiveness of the first therapy mode.

8. The method of claim 7, wherein the command further specifies a switch condition that causes the respiratory therapy device to switch from the second therapy mode to the first therapy mode.

9. The method of claim 7, further comprising:
   automatically updating the mode parameters of the second therapy mode based on usage information gathered during therapeutic usage of the second therapy mode.

10. The method of claim 7, wherein the usage information received from the respiratory therapy device further represents a respiratory disturbance index, and wherein the one or more mode parameters are determined based on the respiratory disturbance index.

11. The method of claim 7, wherein the first therapy mode comprises one of a CPAP mode, and wherein the second therapy mode comprises a volume control mode, the second therapy mode being different from the first therapy mode.

12. A system for configuring respiratory therapy modes for users of respiratory therapy devices, the system comprising:
   means for receiving usage information from a respiratory therapy device, wherein the usage information received from the respiratory therapy device includes:
      a cumulative therapeutic usage time corresponding to a total amount of time the therapy device is used in a first therapy mode,
      a successive therapeutic usage time corresponding to an uninterrupted amount of time the therapy device is used in the first therapy mode, and
      a quality of sleep index indicating effectiveness of the first therapy mode during the successive therapeutic usage time;
   means for determining a first cumulative therapeutic usage threshold amount of time and a second successive therapeutic usage threshold amount of time; and
   means for transmitting a command, responsive to the respiratory therapy device being used in at least the first cumulative therapeutic usage threshold amount of time, and the respiratory therapy device being used in the first therapy mode for at least the second successive therapeutic usage threshold amount of time, wherein the command causes the respiratory therapy device to switch from the first therapy mode to a second therapy mode, wherein the command further dictates one or more mode parameters of the second therapy mode for the respiratory therapy device, and wherein the one or more mode parameters are determined based on the quality of sleep index and the effectiveness of the first therapy mode.

13. The system of claim 12, wherein the command further specifies a switch condition that causes the respiratory therapy device to switch from the second therapy mode to the first therapy mode.

14. The system of claim 12, further comprising: means for automatically updating the mode parameters of the second therapy mode based on usage information gathered during therapeutic usage of the second therapy mode.

15. The system of claim 12, wherein the received usage information further represents a respiratory disturbance index, and wherein the one or more mode parameters are determined based on the respiratory disturbance index.

16. The system of claim 12, wherein the first therapy mode comprises a CPAP mode, and wherein the second therapy mode comprises a volume control mode, the second therapy mode being different from the first therapy mode.

* * * * *